United States Patent [19]
Richter

[11] Patent Number: 5,738,840
[45] Date of Patent: Apr. 14, 1998

[54] ORAL RINSE AND METHOD OF TREATING HALITOSIS

[75] Inventor: Jon L. Richter, Philadelphia, Pa.

[73] Assignee: Profresh Properties, Inc., Philadelphia, Pa.

[21] Appl. No.: 801,106

[22] Filed: Feb. 14, 1997

Related U.S. Application Data

[63] Continuation of Ser. No. 366,087, Dec. 29, 1994, abandoned, which is a continuation-in-part of Ser. No. 224,642, Apr. 7, 1994, abandoned.

[51] Int. Cl.⁶ .................. A61K 7/20; A61K 33/20
[52] U.S. Cl. .................. 424/53; 424/661; 424/662
[58] Field of Search .................. 424/53, 661, 662

[56] References Cited

U.S. PATENT DOCUMENTS

| | | | |
|---|---|---|---|
| Re. 31,779 | 12/1984 | Alliger | 252/187.23 |
| 3,271,242 | 9/1966 | McNicholas et al. | 167/17 |
| 4,013,761 | 3/1977 | Ward et al. | 423/477 |
| 4,104,190 | 8/1978 | Hartshorn | 252/187 |
| 4,143,115 | 3/1979 | Ward et al. | 422/113 |
| 4,234,446 | 11/1980 | Ramras | 252/187 |
| 4,247,531 | 1/1981 | Hicks | 423/477 |
| 4,296,103 | 10/1981 | Laso | 424/130 |
| 4,317,814 | 3/1982 | Laso | 424/130 |
| 4,334,610 | 6/1982 | Ota et al. | 206/205 |
| 4,507,285 | 3/1985 | Kuhne | 424/130 |
| 4,552,679 | 11/1985 | Schubel et al. | 252/90 |
| 4,671,972 | 6/1987 | Schubel et al. | 427/313 |
| 4,689,169 | 8/1987 | Mason et al. | 252/187.24 |
| 4,689,215 | 8/1987 | Ratcliff | 424/53 |
| 4,690,772 | 9/1987 | Tell et al. | 252/106 |
| 4,696,811 | 9/1987 | Ratcliff | 424/52 |
| 4,786,492 | 11/1988 | Ratcliff | 424/53 |
| 4,788,053 | 11/1988 | Ratcliff | 424/53 |
| 4,792,442 | 12/1988 | Ratcliff | 424/53 |
| 4,808,389 | 2/1989 | Ratcliffe | 424/52 |
| 4,818,519 | 4/1989 | Ratcliff | 424/53 |
| 4,837,009 | 6/1989 | Ractliff | 424/53 |
| 4,851,213 | 7/1989 | Ratcliff | 424/53 |
| 4,855,135 | 8/1989 | Ratcliff | 424/127 |
| 4,886,657 | 12/1989 | Ratcliff | 415/53 |
| 4,889,714 | 12/1989 | Ratcliff | 424/53 |
| 4,891,216 | 1/1990 | Kross et al. | 424/78 |
| 4,925,656 | 5/1990 | Ratcliff | 424/53 |
| 4,975,285 | 12/1990 | Ratcliff | 424/661 |
| 4,986,990 | 1/1991 | Davidson et al. | 424/665 |
| 5,006,326 | 4/1991 | Mayurnik et al. | 423/477 |
| 5,008,096 | 4/1991 | Ringo | 423/479 |
| 5,114,647 | 5/1992 | Levesque et al. | 264/115 |
| 5,165,910 | 11/1992 | Oikawa et al. | 423/477 |
| 5,185,161 | 2/1993 | Davidson et al. | 424/665 |
| 5,192,459 | 3/1993 | Tell et al. | 252/106 |
| 5,200,171 | 4/1993 | Ratcliff | 424/52 |
| 5,258,171 | 11/1993 | Eltomi | 423/477 |

Primary Examiner—Shep K. Rose
Attorney, Agent, or Firm—Panitch Schwarze Jacobs & Nadel, P.C.

[57] ABSTRACT

An aqueous composition for the treatment and prevention of malodor of the oral cavity has molecular chlorine dioxide at a concentration of about 1 ppm to about 200 ppm and a pH in the range of about 5.0 to about 7.5. The oral rinse may be used as part of a specific regimen of professional care and/or home use. The oral rinse may be prepared by mixing sodium hypochlorite or other chlorine-releasing agent with sodium chlorite. A convenient kit for preparing the oral rinse treatment contains aqueous sodium chlorite and aqueous sodium hypochlorite in buffered solutions.

20 Claims, 2 Drawing Sheets

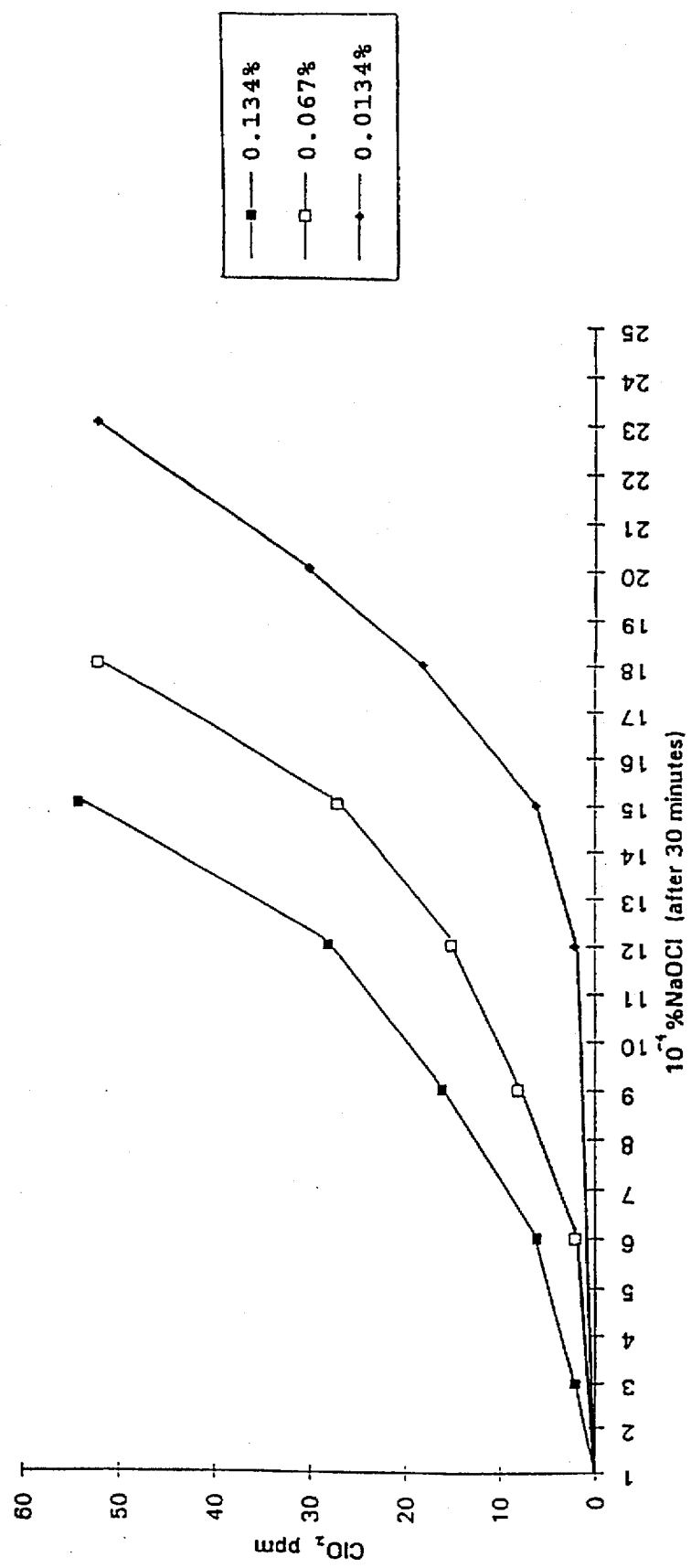

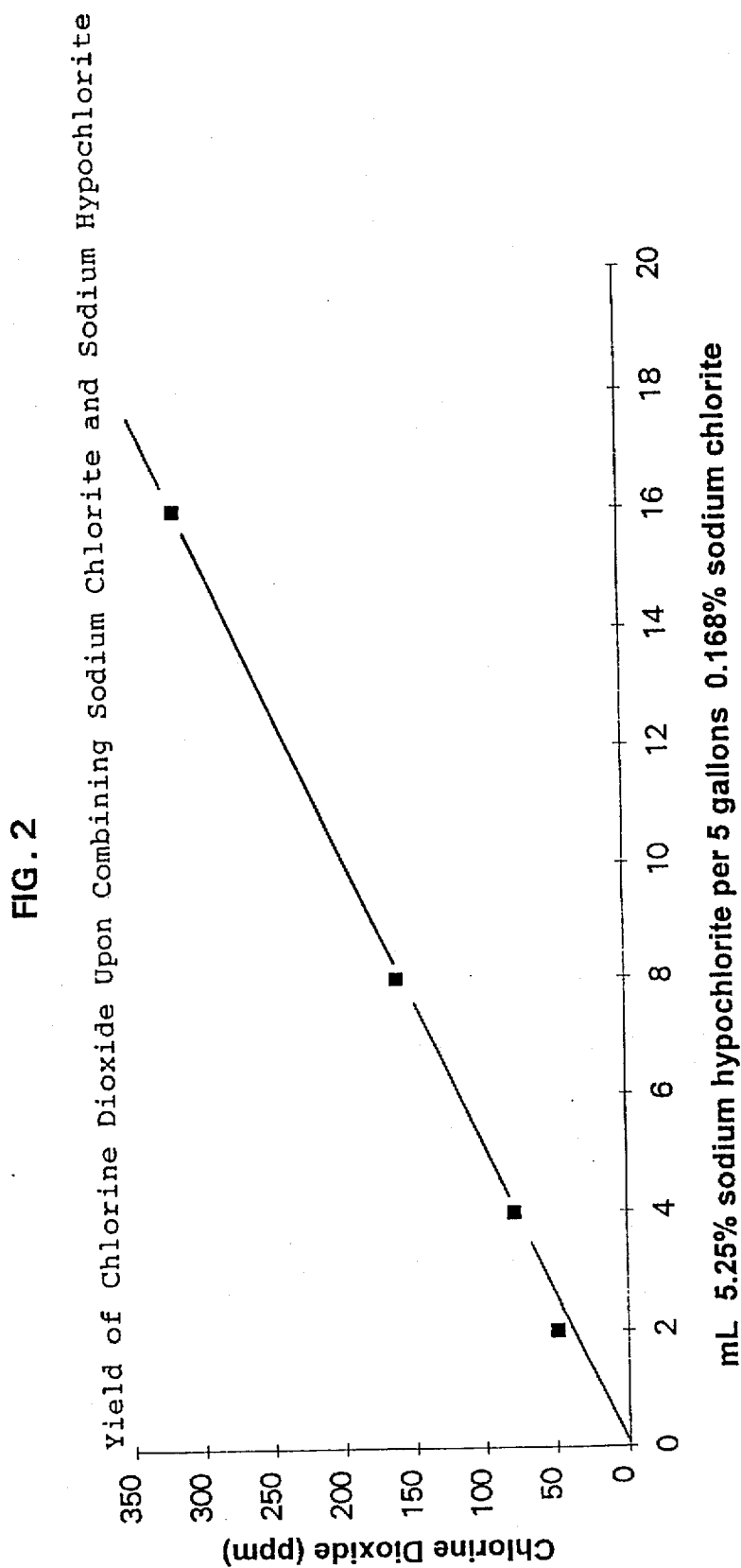

ORAL RINSE AND METHOD OF TREATING HALITOSIS

This application is a continuation of application Ser. No. 08/366,087, filed Dec. 29, 1994, which in turn is a continuation-in-part application of application Ser. No. 08/224,642, filed Apr. 7, 1994 both now abandoned.

FIELD OF THE INVENTION

The invention is generally directed to compositions and their method of use in oral hygiene, and more specifically directed to oral rinse treatments for remediation of halitosis, and to methods of using the oral rinse treatment as part of a daily regimen to eliminate or reduce halitosis. The invention is also directed to a kit containing ingredients with which to prepare the oral rinse treatment.

BACKGROUND OF THE INVENTION

Malodor of the oral cavity, also known as halitosis or bad breath, is an undesirable condition for many people. It is generally believed that a significant cause of such malodor is the presence of anaerobic bacteria at the back of the tongue. The bacteria generate volatile sulfur compounds by degrading sulfur-containing amino acids present in the mouth, and the exhalation of the volatile sulfur compounds is perceived as bad breath.

The prior art has attempted to treat halitosis through methods whereby the oral cavity is rinsed with an aqueous solution of stabilized chlorine dioxide. Examples include U.S. Pat. Nos. 5,200,171; 4,975,285; 4,925,656; 4,889,714; 4,886,657; 4,855,135; 4,851,213; 4,837,009; 4,818,519; 4,808,389; 4,792,442; 4,788,053; 4,786,492; 4,696,811; and 4,689,215, all issued to Perry A. Ratcliff.

The expression "stabilized chlorine dioxide" (SCD) as used in the art is actually a misnomer. In fact, SCD is an aqueous solution comprising sodium chlorite and stabilizers to prevent the degradation of sodium chlorite to chlorine dioxide. SCD may be formed by addition of chlorine dioxide to a solution of a peroxy compound, such as sodium persulfate. The reaction of the peroxy compound with chlorine dioxide results in the reduction of the chlorine dioxide to sodium chlorite. Alternatively, bulk sodium chlorite may be added to water along with some stabilizer. Thus, a solution of SCD need not contain any measurable level of chlorine dioxide molecules at all (hereinafter "molecular chlorine dioxide") and generally contains a residual amount of peroxy compound. Depending on the manufacturer, additives such as buffers and surfactants may be present in combination with the sodium chlorite and stabilizer to comprise the SCD solution.

Molecular chlorine dioxide is recognized to be an effective bleach and deodorant, and is used industrially in that capacity. Molecular chlorine dioxide ($ClO_2$) is a water soluble gas with a high oxidation potential. Because of this high oxidative tendency, chlorine dioxide is readily able to oxidize certain chemical groups found in organic compounds. These groups include C=C, —S—H, —S—S—, —S—$CH_3$ and —O—H. Chlorine dioxide is effective as a bleach and deodorant because common malodorants contain these or other readily oxidizable groupings in their compounds, which are vulnerable to the oxidizing action of chlorine dioxide. Upon oxidation, mercaptans, sulfides and disulfides lose most if not all of their malodor properties.

Chlorine dioxide is an unstable molecule when dissolved in water of near-neutral pH. In aqueous solutions having a pH of about 6 to about 8, chlorine dioxide deteriorates rapidly to the chlorite and chlorate ions (i.e. $2[Cl^{+4}] \rightarrow Cl^+ 3 + Cl^{+5}$). The instability of aqueous chlorine dioxide has limited its utility to those applications where the aqueous chlorine dioxide can be used a) at a specific concentration immediately upon its formation, or b) during the time period when sufficient chlorine dioxide exists, in a continuously degrading solution, to effect its intended task. Depending upon the composition of the chlorine dioxide solution, this time period can range from minutes to many weeks.

Any deodorizing ability of SCD solutions is presumed to result from the conversion of sodium chlorite back to chlorine dioxide. This may occur through either slow degradation of sodium chlorite in the SCD solution, or by reaction of sodium chlorite with acidity in an environment to which the SCD solution is exposed. In fact, at the pH of certain SCD products for oral use, ca. 6.2–7.0, any molecular chlorine dioxide which forms by degradation of the chlorite is converted back to chlorite by reaction with the residual stabilizer, e.g., peroxy compound, present in the SCD solution.

Thus, while SCD is typically characterized in terms of its chlorine dioxide content, it is well-recognized in the art that such a chlorine dioxide content is equivalent to the maximum amount of molecular chlorine dioxide which could be formed upon acidification of SCD, and is not equal to the molecular chlorine dioxide concentration actually present in the solution of SCD.

SCD, in concentrations between 0.05% and 0.1% (of potentially formable molecular $ClO_2$), is reportedly a component in several commercially-available oral hygiene products. As determined by the chlorophenol-red spectrophotometric test, these products contain less than 0.1 parts per million (ppm) of molecular chlorine dioxide, while containing as much as 1340 ppm of sodium chlorite (for the 0.1% product). A concentration of 0.1 ppm, which is equivalent to 0.1 mg/liter, is the approximate amount that can be found in the tap water of municipalities that use $ClO_2$ treatment systems. No measurable deodorant or antibacterial effect for chlorine dioxide has been reported to occur at this concentration. There is no scientific evidence that any of the existing SCD products have any effect on breath malodor when used as directed.

SCD is a rather expensive source for sodium chlorite to be used as a precursor to chlorine dioxide. This is due in part to the presence of the stabilizer, e.g., peroxy compound, which is present in SCD and which acts to return molecular chlorine dioxide to sodium chlorite. Because of the instability of molecular chlorine dioxide in solution, and because of the problems in obtaining chlorine dioxide from SCD, no product has become commercially available which is capable of providing significant and relatively constant levels of molecular chlorine dioxide sufficient to be effective in the reduction or elimination of halitosis by oxidation of malodorant molecules in the oral cavity. Therefore a need still exists for an effective means of treatment of halitosis by the dental practitioner or for home use.

SUMMARY OF THE INVENTION

The present invention provides a composition for the treatment and prevention of malodor of the oral cavity. The composition comprises an aqueous solution of metal chlorite salt and molecular chlorine dioxide, said molecular chlorine dioxide being present at a concentration of about 1 ppm to about 200 ppm and at a pH of about 5.0 to about 7.5 in the composition. A buffering agent is preferably present in the solution to provide the desired pH. The solution of chlorine dioxide is preferably formed from reaction of at least one chlorite metal salt and at least one metal hypochlorite salt, and thus the solution will generally contain some metal hypochlorite salt in addition to the chlorite salt.

The invention also provides a method of forming a solution for an oral rinse treatment comprising the step of combining water, a metal chlorite salt and a metal hypochlorite salt. In a preferred embodiment of the method and composition of the invention, the metal chlorite salt is sodium chlorite and the metal hypochlorite salt is selected from the group consisting of sodium hypochlorite and calcium hypochlorite. The molar ratio of metal hypochlorite salt to metal chlorite salt is preferably about $10^{-7}:1$ to about $10^1:1$.

Another aspect of the invention is a method of treating a person for halitosis, comprising rinsing the person's oral cavity with an oral rinse solution comprising the composition set forth above. In a preferred embodiment, the method further comprises the step of physically removing superficial layers of bacteria and related debris from the oral cavity, which may be accomplished with either a high-pressure spray of said composition or an ultrasonic debridement. Depending on the person's history, the concentration of chlorine dioxide in the oral rinse solution may be varied from about 1 to about 3 ppm, generally for a daily treatment regimen, or from about 10 to about 30 ppm, generally for an initial treatment.

Yet another aspect of the invention is a kit for forming an oral rinse treatment solution comprising (a) water (b) a chlorine-releasing oxidant selected from the group consisting of metal hypochlorite salt and sodium dichloroisocyanurate, (c) a metal chlorite salt, and (d) a buffering agent, wherein upon combining (a), (b), (c) and (d), a solution of molecular chlorine dioxide is produced having a concentration of molecular chlorine dioxide of about 1 ppm to about 200 ppm.

In a preferred embodiment, the kit comprises (a) about 1 part of an aqueous solution comprising sodium hypochlorite at a concentration of about 5.25%, and (b) about 5,000 to about 20,000 parts of an aqueous solution of sodium chlorite at a concentration of about 0.01% to about 0.2%.

BRIEF DESCRIPTION OF THE DRAWINGS

The foregoing summary, as well as the following detailed description of the preferred embodiments of the invention, will be better understood when read in conjunction with the appended drawings. In the drawings:

FIG. 1 is a chart plotting the concentration of molecular chlorine dioxide produced in SCD solutions having the equivalent indicated concentrations of sodium chlorite, as measured 30 minutes after addition of varying quantities of aqueous sodium hypochlorite solution to the SCD solutions.

FIG. 2 is a chart plotting the concentration of molecular chlorine dioxide produced in 5 gallons of 0.168% aqueous sodium chlorite solution, as measured 24 hours after addition of the indicated quantities of 5.25% aqueous sodium hypochlorite to the sodium chlorite solution.

DETAILED DESCRIPTION OF THE PREFERRED EMBODIMENTS

The present invention provides an oral rinse solution comprising an aqueous solution of molecular chlorine dioxide, effective for reducing or minimizing halitosis. The oral rinse treatment of the invention enables one to convey to a person's mouth an effective amount of molecular chlorine dioxide ($ClO_2$) to deodorize the person's breath. The achieved deodorization is believed to occur through the oxidation of odor bodies in the breath, and particularly the sulfur-containing odor bodies which are a major causative factor of bad breath. The inventive oral rinse is an aqueous solution of molecular chlorine dioxide, formed by combining a metal hypochlorite, such as sodium hypochlorite, and a metal chlorite, such as sodium chlorite, at a pH of about 5.0 to about 7.5.

As used herein, the term "molecular chlorine dioxide" refers exclusively to a molecule having the formula $ClO_2$. Aqueous chlorine dioxide refers to an aqueous solution of molecular chlorine dioxide, possibly but not necessarily including other oxychlorine species such as chlorite and chlorate. The term "stabilized chlorine dioxide" is given its standard meaning, which is an aqueous solution predominating in sodium chlorite ($NaClO_2$), with lesser amounts of sodium chlorate ($NaClO_3$), sodium chloride (NaCl) and at least one stabilizer to either retard degradation of sodium chlorite to chlorine dioxide or re-convert the chlorine dioxide degradation product back to sodium chlorite.

The term metal hypochlorite salt, or hypochlorite metal salt, or metal hypochlorite, as used herein, refers to a molecule of the formula $M^1(OCl)_c$, where $M^1$ is a metal cation, c is the valence of the metal and is the number of hypochlorite ligands joined to $M^1$. Exemplary metal hypochlorite salts include, without limitation, sodium hypochlorite and calcium hypochlorite. Sodium hypochlorite, when dissolved in water, is commonly known and referred to herein as bleach.

The term metal chlorite salt, or chlorite metal salt, or metal chlorite, as used herein, refers to a molecule of the formula $M^2(ClO_2)_d$, where $M^2$ is a metal cation, d is the valence of $M^2$ and is the number of chlorite ligands joined to $M^2$. An exemplary metal chlorite includes, without limitation, sodium chlorite.

The reaction product of a metal chlorite salt and a metal hypochlorite salt is molecular chlorine dioxide. According to the inventor's best understanding, the metal hypochlorite salt serves to oxidize the metal chlorite, and thereby form chlorine dioxide.

In a preferred embodiment of the invention, an aqueous solution of sodium chlorite is combined with an aqueous solution of sodium hypochlorite at an appropriate pH and concentrations of reactants. Sodium chlorite is available commercially as a technical grade powder or flake, and as an aqueous liquid concentrate in a range of concentrations. Sodium chlorite is also available in SCD solution, generally in admixture with stabilizing components, such as peroxy compounds. An exemplary solution of sodium chlorite is sold by Vulcan Chemicals under the name "31% Active Sodium Chlorite Solution". An exemplary stabilized chlorine dioxide is sold by International Dioxcide, Inc. under the trademark Anthium Dioxcide, and has a concentration of 5%. The sodium chlorite according to the invention is preferably free of stabilizing compounds, such as peroxy compounds, and is free of organic solvents.

When using a solution of SCD, one should understand that the stated concentration, e.g., 5%, refers to the level of molecular chlorine dioxide which is maximally available in the solution following acidification of the sodium chlorite contained therein. The level of sodium chlorite corresponding to the 5% level of liberatable $ClO_2$ can be either 6.7%, if one simply considers the molecular weight of the two species, or 8.4%, if the additional factor of 80% maximum release efficiency of molecular $ClO_2$ is considered.

The aqueous solution of sodium hypochlorite is commercially available, and is often called bleach or household bleach. An exemplary solution of sodium hypochlorite is available from the Clorox Company, under the trademark CLOROX®, and has a concentration of sodium hypochlorite of 5.25%. Calcium hypochlorite, which is a solid, is available from, for example, Aldrich Chemical Co., Milwaukee, Wis.

If stabilized chlorine dioxide is used as the source of sodium chlorite, it is necessary, in one sense, to "destabilize" it by first overriding its ability to reconvert any molecular chlorine dioxide it forms back to chlorite. The use of a metal hypochlorite according to the invention accomplishes this goal by creating more molecular chlorine dioxide from the chlorite than can be handled by the stabilizers in that SCD solution. Thus, the use of SCD as a metal chlorite source typically necessitates the use of a larger quantity of metal hypochlorite than would be the case if a metal chlorite were used that was free of stabilizing agents.

The oral rinse will generally, but not necessarily, contain additional levels of residual sodium chlorite. This reservoir allows for a continuous low-level creation of molecular chlorine dioxide, through decomposition of small levels of chlorous acid present in the mildly acid solution. This contributes to the replenishment of the molecular chlorine dioxide which gradually decomposes in these solutions. The level of chlorite and pH can be selected so as to maintain a relatively constant level of molecular chlorine dioxide, for an extended period of time, as necessary for an effective and commercially-viable oral rinse solution.

The desired pH of the solution can be achieved through the use of citric acid or any other organic or mineral protic acid, known to those skilled in the art as appropriate for the creation of a buffered solution at the requisite pH of about 5.0 to about 7.5. Other acids which may be used, for example, include phosphoric acid and acetic acid.

In a preferred method of preparing the oral rinse of the invention, it is convenient to use sodium chlorite in water at a concentration of about 0.05% to about 0.2%, and at a pH of about 5.0 to about 7.5. Since all forms of the aqueous sodium chlorite which are available commercially are typically sold at concentrations above the 0.01%–0.2% range, dilution with water, preferably deionized or distilled, is usually necessary prior to combining with the metal hypochlorite. When SCD solutions are used, and they are diluted with water to nominal levels of stabilized chlorine dioxide of less than ca. 0.2%, the amount of molecular chlorine dioxide in that solution will be less than 0.2 ppm.

The oral rinse treatment of the invention has a concentration generally of about one to about two hundred ppm molecular chlorine dioxide, typically from about one to about fifty ppm, and preferably has a concentration of about one to about 30 ppm molecular chlorine dioxide. The desired concentration of molecular chlorine dioxide in the oral rinse solution of the invention will be in part determined by the protocol being performed. That is, a concentration of only 1–3 ppm may be sufficient for a daily maintenance program. However, a concentration of 10–30 ppm may be appropriate for a first-time treatment, under the supervision of a trained practitioner or when conducted by the patient.

PREPARATIVE EXAMPLES

When working with about 16 ounces of a solution of aqueous sodium chlorite at concentrations of about 0.05% to about 0.2%, and a pH of about 6.2 to about 6.6, an effective odor-suppressing concentration of molecular chlorine dioxide may be produced by adding to the aqueous sodium chlorite solution about 1.0 to about 5.0 milliliters of sodium hypochlorite having a concentration of about 0.1% to about 5.25%. To prepare an oral rinse especially for beginning treatment at home by a consumer, and for professional oral debridement, 2 milliliters of 5.25% NaOCl is added to a five-gallon container containing 0.05% to about 0.2% aqueous sodium chlorite at a pH of about 6.0 to about 6.4, to yield an oral rinse having 10–30 ppm of molecular chlorine dioxide. To prepare an oral rinse especially for long-term treatment to reduce breath malodor, preferably 1 milliliter of 5.25% NaOCl is added to a five-gallon container of about 0.05%–0.2% $NaClO_2$ to provide an oral rinse treatment having about 1 to about 3 ppm $ClO_2$.

An alternative method to prepare the oral rinse of the invention is to add tablets comprising calcium hypochlorite or a chlorine-releasing substance, such as sodium dichloroisocyanurate, and a protic acid, to an aqueous solution of sodium chlorite. The protic acid serves to first acidify the solution, and then serves as a buffering agent. The buffering agent is typically an organic acid such as citric acid. The sodium chlorite, buffering agent, and hypochlorite-releasing substance should be combined in a tightly sealed container, and shaken gently to mix them together. The mixing together of these components preferably occurs under standard room conditions of temperature and atmospheric pressure, i.e. about 25° C. and about 1 atmosphere of pressure, and allowed to remain for ¼–6 hours.

The resulting solution should be stored in a tightly sealed container, of a composition and thickness which would make it impervious to the passage of molecular chlorine dioxide, in order to retard its escape from the solution and the headspace above the solution. Upon formation, this composition provides a level of molecular chlorine dioxide which is preferably about one to about two hundred parts per million (ppm), and more preferably about one to about fifty ppm, of molecular chlorine dioxide, with an effective shelflife of about one week to about three months.

It should be emphasized that the concentration range of about one to about two hundred ppm molecular chlorine dioxide refers to the actual concentration, by weight, of chlorine dioxide molecules in the solution which is to be placed in the mouth, and does not refer to the concentration of molecular chlorine dioxide which could theoretically be released upon lowering the pH of the sodium chlorite or a stabilized chlorine dioxide solution.

A wide variety of concentrations of molecular chlorine dioxide can be achieved with the present invention depending upon the circumstances of use, and the invention should not be so limited thereby. The concentration of molecular chlorine dioxide in the oral rinse treatment of the invention can be modulated by varying the pH and concentration of the original solution of sodium chlorite and varying the quantity and concentration of hypochlorite added thereto. More chlorine dioxide will be generated as the concentration of metal hypochlorite is increased for a constant amount of metal chlorite, or as the pH of the metal chlorite solution is lowered.

The relationship between formation of molecular chlorine dioxide and reaction of sodium chlorite and sodium hypochlorite can be seen in FIGS. 1 and 2. In FIG. 1, three concentrations of SCD (0.1%, 0.05% and 0.01%, corresponding to 0.134%, 0.167% and 0.139% respectively, of sodium chlorite) were studied for the amount of chlorine dioxide they generated upon addition thereto of a sodium hypochlorite solution. The concentration of sodium hypochlorite initially present in the mixture of sodium chlorite and sodium hypochlorite is indicated on the x-axis of FIG. 1. FIG. 1 shows the approximate amounts of sodium chlorite and sodium hypochlorite that should be combined to form a desired concentration of molecular chlorine dioxide, where the molecular chlorine dioxide concentration is determined 30 minutes after combining the two reactants.

In FIG. 2, varying quantities of 5.25% sodium hypochlorite are added to a 5 gallon solution of 0.168% sodium chlorite, at a pH of 6.0. The sodium chlorite solution of FIG. 2 was not prepared by dilution of SCD, as was done to provide the sodium chlorite solutions of FIG. 1. Thus, there were not stabilizers, e.g., peroxy compounds, in the sodium chlorite solutions of FIG. 2. Twenty four hours after combining the sodium hypochlorite and sodium chlorite, the concentration of molecular chlorine dioxide in the resulting solutions were determined. The higher concentrations of molecular chlorine dioxide reported in FIG. 2, as compared to FIG. 1, result in part from the higher relative quantities of bleach used. To prepare useful, odor-suppressing solutions of molecular chlorine dioxide, the molar ratio of metal hypochlorite salt to metal chlorite salt should be about $10^{-7}:1$ to about $10^1:1$.

The ability of a composition prepared by combining metal chlorite and metal hypochlorite to provide stable levels of molecular chlorine dioxide according to the invention, can be seen by reference to TABLES 1 and 2. A composition, characterized in TABLE 1, was prepared by combining 0.13 mL of 5.25% sodium hypochlorite, 8 ounces of a 0.1% solution of SCD, and citric acid to bring the pH to 6.0. A composition, characterized in TABLE 2, was prepared by adding 0.3 mL 5.25% sodium hypochlorite, 16 ounces of 0.1% SCD and citric acid to bring the pH to 6.4.

TABLE 1

| 8 oz Bottle | 1 Week | 2 Weeks | 3 Weeks | 4 Weeks |
|---|---|---|---|---|
| Chlorine Dioxide (ppm) | 19.0 | 18.7 | 18.4 | 18.4 |
| Chloride (ppm) | 80.1 | 91.8 | 88.6 | 91.0 |
| Chlorite (ppm) | 1566 | 1608 | 1649 | 1449 |
| Chlorate (ppm) | 65.5 | 67.0 | 70.7 | 74.5 |

TABLE 2

| 16 oz Bottle | 1 Week | 2 Weeks | 3 Weeks | 4 Weeks |
|---|---|---|---|---|
| Chlorine Dioxide (ppm) | 8.80 | 8.53 | 8.31 | 8.30 |
| Chloride (ppm) | 72.6 | 85.4 | 84.5 | 88.0 |
| Chlorite (ppm) | 1786 | 1750 | 1703 | 1527 |
| Chlorate (ppm) | 62.3 | 63.1 | 63.5 | 63.7 |

The data in TABLES 1 and 2 clearly show that sustainable levels of molecular chlorine dioxide, in excess of 1 ppm, can be achieved over a period of at least 4 weeks according to the procedures described herein.

The concentrations reported in FIGS. 1 and 2, and in TABLES 1 and 2, were measured spectrophotometrically, using a wavelength of 360 nm. Molecular chlorine dioxide has an extinction coefficient of 1242 liter/mol-cm.

After formation, the shelf life of the oral rinse treatment solution will vary to a significant degree in direct proportion to the concentration of $NaClO_2$ in the final solution, and inversely with the concentration of $ClO_2$ and the pH in the final solution. In other words, as the concentration of molecular chlorine dioxide in the oral rinse increases, the shelf-life of the rinse will tend to decrease. This occurs because the rate of generation of molecular chlorine dioxide from the chlorite in solution can not ordinarily keep pace with the decomposition of higher levels of the chlorine dioxide already formed.

Nevertheless, even though the rate of decrease in the concentration of chlorine dioxide will be greater for a higher concentration $ClO_2$ solutions than for lower concentration solutions, the potential use life of say, a 50 ppm solution may be greater than a 5 ppm solution (since, after the 50 ppm solution degrades to 5 ppm, the 5 ppm solution may continue to be useful for different applications). In addition, as the concentration of sodium chlorite in the oral rinse is increased, the shelf life will increase because of the higher reserve capacity of the chlorine dioxide-generating chlorite. Under typical conditions, the oral rinse treatment has an effective lifetime of about 3 weeks to about 3 months, when stored in a tightly sealed, impervious container at room temperature.

The container in which the mixing occurs should be completely filled with solution and sealed. After mixing, the solution should stand undisturbed and sealed for at least about one hour before use. A stable level of $ClO_2$ is attained within twelve hours; however a usable concentration is obtained within about one hour. It has been discovered that the oral rinse treatment of the invention advantageously provides for the slow but longterm formation of molecular chlorine dioxide, within concentration levels of about 1 to about 200 ppm.

To provide convenience to the consumer, the oral rinse of the invention can be prepared at the point of end-use by application of a kit. The kit comprises metal chlorite, a chlorine-releasing oxidant such metal hypochlorite and/or dichloroisocyanurate, water and a buffering agent. In a preferred embodiment, the hypochlorite is present as a powder or tablet, and the metal chlorite is present as an aqueous solution of sodium chlorite, in amounts and concentrations such that upon mixing all the buffering agent, sodium chlorite solution and hypochlorite in the kit, a solution of molecular chlorine dioxide is produced having a concentration of molecular chlorine dioxide of about 1 ppm to about 200 ppm, and preferably about 1 ppm to about 50 ppm.

The hypochlorite may also be present in the kit as an aqueous solution. In a preferred embodiment, the kit contains a solution comprising sodium hypochlorite dissolved in 2 milliliters of water at a concentration of about 5.25%, and a 5-gallon solution comprising sodium chlorite dissolved in water at a concentration of about 0.01% to about 0.2%, so that upon mixing the two solutions about 5 gallons of solution are prepared. Proportionately smaller volumes of reactants should be used to prepare, say, a 16 oz. container for convenient home use.

As one embodiment of the invention, the hypochlorite and buffering agent, such as sodium hypochlorite and citric acid, respectively, may be stored in the cap of a container of aqueous sodium chlorite. The user may introduce the hypochlorite and buffering agent into the sodium chlorite solution simply by twisting the cap. In this configuration, the essential components of the oral rinse of the invention may be stored for an extended period of time, and then the oral rinse of the invention can be readily formed when desired. Alternatively, aqueous solutions of metal hypochlorite, buffering agent, and metal chlorite may be packaged and sold together in other configurations.

With the previously described method for producing a chlorine dioxide-containing solution just prior to use, the present invention provides a product which has the extended shelf life necessary for retail distribution, and which has a higher potency than any currently available molecular chlorine dioxide containing product. The present invention enables a product to be distributed with a nearly indefinite shelf life, yet retains the ability to produce effective, odor-suppressing amounts of molecular chlorine dioxide, a combination of attributes heretofore not previously recognized or attained.

Research conducted with the oral rinse of the invention having 1–3 ppm molecular chlorine dioxide, has demonstrated that a specific regimen of daily debridement of the hard and soft tissues of the mouth immediately followed by rinsing of the mouth with the oral rinse, produces a dramatic and long-lasting reduction of breath malodor in patients suffering from common chronic halitosis. This effect has been demonstrated in over 500 test subjects who were evaluated for breath malodor organoleptically and/or instrumentally pre- and post-treatment for periods of up to eight months.

By utilizing the oral rinse of the present invention for a predetermined time period, one can effectively treat halitosis. For example, a twice daily regimen of rinsing with the oral treatment solution in combination with physical debridement of intraoral tissue surfaces for 1 minute or more, as needed, followed by interdental cleaning, scraping of the back top surface of the tongue and re-rinsing for 30 seconds with the oral rinse, effectively reduces oral cavity malodor for extended time periods thereafter.

TREATMENT AND MAINTENANCE PROGRAM

The following is a preferred method of using the chlorine dioxide rinse solution of the invention in a regimen to reduce or eliminate halitosis. The person undergoing treatment for halitosis should preferably utilize the treatment and maintenance program described herein, every morning and evening, although some individuals may perform the regimen more or less frequently to maintain their breath odor-free 24 hours a day.

Users preferably do not use toothpaste or other oral rinses for at least an hour before, or 15 minutes after, using the oral rinse treatment of the present invention. If a person is beginning treatment for breath malodor without professional forced or ultrasonic irrigations, that person may use an 8-ounce starter rinse containing 3–10 ppm $ClO_2$ rinse, which will be used for the first four days. On day five, the user discards any remaining starter rinse and begins the maintenance regimen, using an oral rinse treatment containing 1–3 ppm $ClO_2$. As an alternative to the home starter rinse, the subject may undergo professional oral debridement and lavage with a 10–30 ppm $ClO_2$ irrigant.

As used herein, the term professional oral debridement and lavage includes forced spraying (air and rinse treatment) of all hard and soft tissues of the mouth with a forced-spray dental debrider such as a Prophy Jet (Dentsply). For best results, particular attention should be given to removing bacterial and other debris from the crevices and fissures of the tongue, and in particular the dorsal-posterior of the tongue. The exit of the Prophy Jet should be held approximately 3 mm from the surface to be rinsed, and the rinse should be directed at an approximately 90° angle to the surface. Debridement and lavage with the oral rinse solution should be done around the gingival margins, and between the teeth with a standard ultrasonic device such as a Cavitron (Dentsply).

In the morning and in the evening, a person should take approximately ½-ounce of the $ClO_2$-containing oral rinse into his/her mouth, and vigorously swish the treatment solution around the oral cavity. Then, with the rinse still in the user's mouth, a toothbrush is inserted, keeping the user's lips lightly sealed around the toothbrush handle to avoid spillage. The user tilts his/her head slightly backward and brushes teeth, palate, cheeks, gums and tongue, making sure that the rinse reaches all of these regions. The person then expectorates. The rinse should stay in the person's mouth for one minute, including brushing time. It is advisable that the toothbrush not come into contact with any other product.

Next, and using a tongue blade, the patient cleans the top and back of the tongue to remove the superficial layers of bacterial buildup and debris therefrom. It is especially important to scrape the midline or center of the tongue all the way back to the wart-like bumps that are located on the very back of the tongue. Gagging should be expected. The user should re-wet the tongue with saliva after each scrape, and then swallow. Six to eight scrapes are usually sufficient.

Dental floss such as in a dental floss holder is next used to remove superficial bacteria and debris from between the patient's back teeth. The floss is slid between the user's teeth with a saw-like motion. Once the floss is between two teeth, it is guided up and down the surfaces of each tooth at least five times. That means there are two surfaces to clean each time the patient slides the floss between two teeth.

The patient then rinses their mouth again vigorously with about ¼-ounce of the oral rinse for 30 seconds. The patient should gargle with his/her tongue extended to assure that the oral rinse treatment reaches the back of the tongue. Then expectorate the rinse liquid.

CLINICAL RESULTS

Set forth below are clinical data showing the efficacy of an aqueous molecular chlorine dioxide oral rinse in accordance with the present invention. The solution used in the professional debridement and lavage was prepared using three milliliters of aqueous sodium hypochlorite having a concentration of 5.25% with 5 gallons of sodium chlorite, in the form of stabilized chlorine dioxide diluted to the 0.1% level as SCD (0.134% sodium chlorite), at a pH of 6.4±0.2. The oral rinse so prepared contained 10–20 ppm of molecular $ClO_2$.

Twenty one subjects received treatment consisting of forced irrigation of all oral soft tissues with air, followed by oral contact with the above-described oral rinse, delivered with a Prophy Jet. Particular efforts were made to remove all visible coating from the dorsal-posterior surface of the tongue. Periodontal areas were irrigated with the same solution, but delivered with a Cavitron ultrasonic dental cleaner.

All but seven of the subjects were given instructions in the maintenance program set forth above, and a supply of oral rinse treatment having 1–3 ppm $ClO_2$. The seven subjects who were not given instructions in the maintenance program served as controls.

Subjects were evaluated instrumentally with a modified sulfide monitor (Interscan, Chatsworth, Calif.) for concentrations (parts per billion, ppb) of volatile sulfur compounds in mouth air, nasal air and lung air. Subjects were evaluated organoleptically by two judges independently on a scale of 0–5 for malodor of the mouth air, nasal air, lung air, tongue swab, dental floss drawn between the back teeth, and any removable dental appliances ("0" being no detectable malodor, "5" being overwhelmingly offensive malodor.)

These evaluations were performed just before treatment and 12–18 days after treatment for all subjects. Each subject was instructed to refrain from food, drink and oral hygiene for the same number of hours, which was at least 8 hours, before testing for both the pre- and post-treatment evaluations. All subjects were instructed to refrain from smoking, alcohol, garlic, onions, "hot" spices, mouthwashes, antibiotics and scented cosmetics for the same period of time prior to pre- and post-treatment evaluations.

TABLES 3 and 4 show the pre- and post-treatment levels of volatile sulfur compounds in mouth, nasal and lung air, and the large decrease in those compounds when a person is treated in accordance with the present invention. Also shown is the beneficial change in organoleptic assessment as described above. The seven control patients, who did not use the oral rinse treatment in the intervening 12–18 days period, in accordance with the present invention, showed no significant change in either their levels of volatile sulfur compounds or organoleptic assessments.

TABLE 3

Pre-Treatment

| SUBJECT | $VC_M$ | $VC_N$ | $VC_L$ | $Org_M$ | $Org_N$ | $Org_L$ | $Org_t$ | $Org_f$ | $Org_a$ |
|---|---|---|---|---|---|---|---|---|---|
| LR | 735 | 180 | 160 | 3.5 | 0 | 0.5 | 4 | 3 | NA |
| MM | 325 | 160 | 180 | 3 | 0 | 0 | 3 | 2 | NA |
| PF* | 650 | 140 | 150 | 3.5 | 0 | 0 | 4 | 3 | NA |
| JF* | 480 | 120 | 140 | 2 | 0 | 0 | 3 | 2 | NA |
| KL | >1000 | 190 | 230 | 4 | 0 | 1 | 5 | 4 | 2 |
| CB | 285 | 170 | 160 | 2 | 0 | 0 | 3 | 3 | NA |
| PD* | 585 | 200 | 180 | 4 | 0 | 0 | 4 | 4 | NA |
| PL | 780 | 225 | 190 | 3.5 | 0 | 0 | 4 | 3 | NA |
| MJ | 450 | 170 | 190 | 3 | 0 | 0.5 | 3 | 2 | NA |
| BC | >1000 | 220 | 270 | 4.5 | 0.5 | 0.5 | 5 | 4 | NA |
| AL* | 690 | 180 | 180 | 3 | 0 | 0 | 4 | 2 | 1 |
| TS | 340 | 145 | 175 | 4 | 0 | 0 | 3 | 4 | NA |
| PR | 490 | 175 | 190 | 3 | 0 | 0 | 3 | 3 | NA |
| JN | 520 | 195 | 180 | 3 | 0 | 0 | 4 | 4 | NA |
| KF* | 290 | 150 | 175 | 4 | 0 | 0 | 3 | 5 | NA |
| GY | 620 | 200 | 160 | 3 | 0 | 0.5 | 4 | 3 | NA |
| SL | 320 | 210 | 225 | 2 | 0 | 0 | 3 | 2 | NA |
| AX* | 860 | 170 | 170 | 4 | 0 | 0 | 4 | NA | 4 |
| SD | 760 | 140 | 185 | 3.5 | 0 | 0 | 3 | 4 | NA |
| SB | 280 | 180 | 170 | 2 | 0 | 0 | 2.5 | 3 | NA |
| ML | 435 | 125 | 135 | 4 | 0 | 0 | 3 | 3 | NA |

*Control subjects. These subjects underwent treatment in the office but did not practice the home-care regimen after treatment.
$VCA_M$ = Volatile Sulfur Compounds (ppb) in Mouth air
$VCA_N$ = Volatile Sulfur Compounds (ppb) in Nasal air
$VCA_L$ = Volatile Sulfur Compounds (ppb) in Lung air
$Org_M$ = Organoleptic Assessment (0–5) Mouth Air
$Org_N$ = Organoleptic Assessment (0–5) Nasal Air
$Org_L$ = Organoleptic Assessment (0–5) Lung Air
$Org_t$ = Organoleptic Assessment (0–5) tongue sample
$Org_f$ = Organoleptic Assessment (0–5) floss (interproximal dental) sample
$Org_a$ = Organoleptic Assessment (0–5) appliance

TABLE 4

Post-Treatment
2 weeks (12–18 days)

| SUBJECT | $VC_M$ | $VC_N$ | $VC_L$ | $Org_M$ | $Org_N$ | $Org_L$ | $Org_t$ | $Org_f$ | $Org_a$ |
|---|---|---|---|---|---|---|---|---|---|
| LR | 120 | 120 | 115 | 0 | 0 | 0 | 1 | 0 | NA |
| MM | 145 | 145 | 155 | 0 | 0 | 0 | 0 | 1 | NA |
| PF* | 540 | 130 | 125 | 3 | 0 | 0 | 4 | 2 | NA |
| JF* | 510 | 145 | 160 | 3 | 0 | 0 | 3 | 3 | NA |
| KL | 180 | 180 | 180 | 0.5 | 0 | 0 | 1 | 1 | 0 |
| CB | 120 | 125 | 120 | 0 | 0 | 0 | 0 | 0 | NA |
| PD* | 420 | 170 | 180 | 4 | 0 | 0 | 3 | 4 | NA |
| PL | 140 | 120 | 140 | 0 | 0 | 0 | 0 | 0 | NA |
| MJ | 115 | 110 | 120 | 0 | 0 | 0 | 0 | 0 | NA |
| BC | 150 | 140 | 135 | 0 | 0 | 0 | 0.5 | 0 | NA |
| AL* | 760 | 200 | 185 | 3 | 0 | 0 | 4 | 3 | 2 |
| TS | 115 | 115 | 120 | 0 | 0 | 0 | 0 | 0 | NA |
| PR | 160 | 160 | 150 | 0 | 0 | 0 | 0 | 0 | NA |
| JN | 145 | 130 | 130 | 0 | 0 | 0 | 1 | 0 | NA |
| KF* | 380 | 180 | 190 | 3 | 0 | 0 | 4 | 3 | NA |
| GY | 150 | 150 | 160 | 0 | 0 | 0 | 0 | 0 | NA |
| SL | 290 | 170 | 170 | 3 | 0 | 0 | 3 | NA | 4 |
| Ax* | 800 | 150 | 160 | 4 | 0 | 0.1 | 4 | 4 | NA |
| SD | 120 | 120 | 120 | 0 | 0 | 0 | 0 | 0 | NA |
| SB | 160 | 170 | 160 | 0 | 0 | 0 | 0 | 0 | NA |
| ML | 190 | 180 | 180 | 0 | 0 | 0 | 0 | 0 | NA |

*Control subjects. These subjects underwent treatment in the office but did not practice the home-care regimen after treatment.
$VCA_M$ = Volatile Sulfur Compounds (ppb) in Mouth air
$VCA_N$ = Volatile Sulfur Compounds (ppb) in Nasal air
$VCA_L$ = Volatile Sulfur Compounds (ppb) in Lung air
$Org_M$ = Organoleptic Assessment (0–5) Mouth Air
$Org_N$ = Organoleptic Assessment (0–5) Nasal Air
$Org_L$ = Organoleptic Assessment (0–5) Lung Air
$Org_t$ = Organoleptic Assessment (0–5) tongue sample
$Org_f$ = Organoleptic Assessment (0–5) floss (interproximal dental) sample
$Org_a$ = Organoleptic Assessment (0–5) appliance It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for the treatment and prevention of malodor of the oral cavity, or halitosis, comprising rinsing the oral cavity with an aqueous solution of molecular chlorine dioxide and a metal chlorite salt, said metal chlorite salt being present in an amount sufficient to maintain said molecular chlorine dioxide at a concentration of about 3 ppm to about 200 ppm and at a pH of about 5.0 to about 7.5 in the solution, until post-treatment levels of volatile sulfur compounds which cause the malodor are reduced below pre-treatment levels.

2. The method according to claim 1 wherein the solution has a molecular chlorine dioxide concentration of about 3 ppm to about 50 ppm.

3. The method according to claim 1, further comprising a buffering agent to maintain the pH in a range of about 6.0 to about 6.6.

4. The method according to claim 3, wherein the buffering agent is selected from the group consisting of citric acid, phosphoric acid and acetic acid.

5. The method according to claim 1, wherein the metal chlorite salt is present in the solution at a concentration of about 0.01% to about 0.2%.

6. The method according to claim 1, wherein the molecular chlorine dioxide is the reaction product of a metal chlorite salt and a metal hypochlorite salt.

7. The method according to claim 6, wherein the composition is substantially free of stabilizers that either retard the formation of molecular chlorine dioxide from the metal chlorite salt and the metal hypochlorite salt or reconvert molecular chlorine dioxide back to chlorite.

8. The method according to claim 6, wherein the metal chlorite salt comprises sodium chlorite and the metal hypochlorite salt is selected from the group consisting of sodium hypochlorite and calcium hypochlorite.

9. The method according to claim 8, wherein the solution is formed by combining about 1 to about 5 milliliters of an aqueous solution of sodium hypochlorite at a concentration of about 0.13% to about 5.25% with about 8 ounces to about 5 gallons of an aqueous solution of sodium chlorite at a concentration of about 0.05% to about 0.2%.

10. The method according to claim 1, further comprising the step of physically removing superficial layers of bacteria and related debris from the oral cavity.

11. The method according to claim 10, wherein the oral rinse solution has a molecular chlorine dioxide concentration of about 10 to about 30 ppm, and the superficial layers of bacteria and related debris are removed through use of a high pressure spray of said composition.

12. The method according to claim 10, wherein the oral rinse solution has a molecular chlorine dioxide concentration of about 10 to about 30 ppm, and the superficial layers of bacteria and related debris are removed through use of ultrasonic debridement.

13. The method according to claim 10, wherein the oral rinse solution has a molecular chlorine dioxide concentration of about 3 to about 10 ppm.

14. The method according to claim 10, wherein the rinsing is done on a daily basis.

15. A method for the treatment and prevention of malodor of the oral cavity comprising rinsing the oral cavity with an aqueous solution of molecular chlorine dioxide and a metal chlorite salt, wherein the amount of metal chlorite salt and the pH of the solution are selected so as to maintain a continuously effective concentration of about 3 to about 200 ppm molecular chlorine dioxide for a period of time sufficient to provide an effective and commercially-viable oral rinse solution.

16. The method according to claim 15, wherein the pH is about 6.0 to about 6.6 and the period of time is about one week to about 3 months.

17. The method according to claim 15, wherein the metal chlorite salt is provided in the solution as stabilized chlorine dioxide, and the solution further comprises sufficient metal hypochlorite to override stabilizers in the stabilized chlorine dioxide and to create and maintain an effective concentration of molecular chlorine dioxide.

18. The method according to claim 15, wherein the solution is substantially free of stabilizing compounds which maintain the metal chlorite salt.

19. The method of claim 15, wherein the composition is substantially free of organic solvents.

20. The method according to claim 15, wherein the concentration of molecular chlorine dioxide is sufficient to oxidize sulfur-containing odor bodies in the breath from the oral cavity.

* * * * *